(12) United States Patent
Rosenberg et al.

(10) Patent No.: US 9,095,699 B2
(45) Date of Patent: Aug. 4, 2015

(54) SYSTEM FOR NERVE SENSING AND STIMULATION EMPLOYING MULTI-ELECTRODE ARRAY

(71) Applicant: Pacesetter, Inc., Sunnyvale, CA (US)

(72) Inventors: Stuart Rosenberg, Castaic, CA (US); Cecilia Qin Xi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/310,950

(22) Filed: Jun. 20, 2014

(65) Prior Publication Data

US 2014/0303685 A1 Oct. 9, 2014

Related U.S. Application Data

(62) Division of application No. 13/442,715, filed on Apr. 9, 2012, now abandoned.

(51) Int. Cl.
*A61N 1/36* (2006.01)
*A61N 1/05* (2006.01)

(52) U.S. Cl.
CPC .......... *A61N 1/0551* (2013.01); *A61N 1/36071* (2013.01); *A61N 1/36125* (2013.01); *A61N 1/36135* (2013.01)

(58) Field of Classification Search
CPC ........... A61N 1/36125; A61N 1/36128; A61N 1/36185
See application file for complete search history.

(56) References Cited

U.S. PATENT DOCUMENTS

| 7,194,313 | B2 | 3/2007 | Libbus |
| 2002/0055764 | A1* | 5/2002 | Malonek et al. ............. 607/122 |
| 2007/0100408 | A1 | 5/2007 | Gerber |
| 2008/0027514 | A1 | 1/2008 | DeMulling |

OTHER PUBLICATIONS

Non-Final Office Action mailed Sep. 16, 2013; Related U.S. Appl. No. 13/442,715.
Final Office Action mailed Feb. 6, 2014: Related U.S. Appl. No. 13/442,715.

* cited by examiner

*Primary Examiner* — Eric D. Bertram
(74) *Attorney, Agent, or Firm* — Theresa A. Raymer (57) ABSTRACT

A nerve stimulation system includes a pulse generator and implantable lead. The pulse generator includes a sensing module and a pace circuit. The lead has an electrode array near the distal end and a connector at the proximal end for connection to the pulse generator. Conductors in the lead electrically connect the electrode array with the sensing module and pace circuit. The electrode array includes a first pair of small electrodes and a large electrode close to each other. The small electrodes and large electrode are physically separated from each other by insulative spaces extending generally transversely to a longitudinal axis of the lead. When the conductors are in electrical communication with the sensing module and pace circuit, the first pair of small electrodes are in electrical communication with both the sensing module and the pace circuit and the large electrode is in electrical communication with the pace circuit only.

16 Claims, 5 Drawing Sheets

SYSTEM FOR NERVE SENSING AND STIMULATION EMPLOYING MULTI-ELECTRODE ARRAY

PRIORITY CLAIM

This application is a Divisional application of U.S. patent application Ser. No. 13/442,715, filed Apr. 9, 2012, entitled "EMPLOYING MULTI-ELECTRODE ARRAY" which is incorporated herein by reference in its entirety to provide continuity of disclosure.

FIELD OF THE INVENTION

Aspects of the present invention relate to medical apparatus and methods. More specifically, the present invention relates to implantable medical leads, pulse generators and related methods.

BACKGROUND OF THE INVENTION

Spinal cord stimulation (SCS) is presently indicated in the US and International markets for treatment of chronic, intractable pain of the trunk and limbs, often due to failed back surgery syndrome or complex regional pain syndrome. In Europe, SCS is also indicated for treatment of intractable angina.

As understanding about mechanisms of pain management increase, and as indications expand to areas such as cardiovascular in which immediate patient perception of pain relief and paresthesias are not indicators of efficacy, it will be desirable to sense neural firing patterns along the spinal cord and peripheral nerves.

At present, nerve recording can only be done during acute studies with highly sensitive instrumentation. Nerve recording is typically enabled with surgically positioned microelectrodes for in situ recordings or with micropipette electrodes for isolated single-nerve patch or voltage clamp recordings.

There is a need in the art for practical, in-vivo recording of neural signals from the spinal cord of a patient.

BRIEF SUMMARY OF THE INVENTION

Disclosed herein is a nerve stimulation system including a pulse generator and an implantable lead. In one embodiment, the pulse generator includes a sensing module and a pace circuit. The implantable lead includes a distal end, an electrode array near the distal end, a proximal end including a lead connector end configured to couple the proximal end to the pulse generator, and conductors extending through the lead from the electrode array and caused to be in electrical communication with the sensing module and pace circuit when the proximal end is coupled to the pulse generator. The electrode array includes at least a first pair of small electrodes and a large electrode in close proximity to each other. The small electrodes and large electrode are physically separated from each other by non-conductive spaces extending generally transversely to a longitudinal axis of the lead. When the conductors are in electrical communication with the sensing module and pace circuit, the first pair of small electrodes are in electrical communication with both the sensing module and the pace circuit and the large electrode is in electrical communication with the pace circuit, but not the sensing module.

Also disclosed herein is a spinal cord stimulation system including a pulse generator and an implantable lead. The implantable lead distally extends from the pulse generator and includes an electrode array near a distal end of the lead. The electrode array includes a pair of small electrodes and a large electrode. The small electrodes are separated from each other by a non-conductive space generally transverse to a longitudinal axis of the lead and having a distal-proximal distance of between approximately 0.05 mm and approximately 2 mm. The large electrode is separated from a closest of the small electrodes by a non-conductive space generally transverse to a longitudinal axis of the lead and having a distal-proximal distance between approximately 0.02 mm and approximately 1 mm. The pulse generator causes the small electrodes to both sense and stimulate and the large electrode to only stimulate. The small electrodes and large electrode operate together during stimulation as a single electrode.

Further disclosed herein is a spinal cord stimulation system including a lead supported electrode array and a pulse generator in electrical communication with the electrode array. The electrode array includes a first pair of small electrodes and a large electrode. The first pair of small electrodes acts as both sensing electrodes and stimulation electrodes. The large electrode only acts as a stimulation electrode. The small electrodes and large electrode act as a single electrode when stimulating.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve a spinal cord stimulation (SCS) system 5 configured to enable sensing of nerve firings. Specifically, the SCS system 5 disclosed herein includes an implantable medical lead 10 having one or more electrode arrays 15, which, along with associated circuitry of a pulse generator 20 of the SCS system 5, enables sensing of nerve firings. Each electrode array 15 has the characteristic of high signal to noise ratio to sense the low-amplitude, high-frequency signal on the nervous system in order to extract signal (firing pattern) characteristics. Neural sensing patterns can then be analyzed in a variety of ways for use in triggering therapy delivery or cessation, modification of programmed parameters, or diagnostic features and alerts. The specialized electrode arrays 15 disclosed herein are particularly suited for percutaneous spinal cord leads. However, the specialized electrode arrays 15 disclosed herein are also applicable to other types of leads and should not be considered as being limited to percutaneous leads. Such electrode arrays 15 are advantageous as a single such electrode array can be used for both neural sensing and for delivery of stimulation pulses, the latter of which may be delivered in a manner substantially like conventional SCS.

Figure 1:
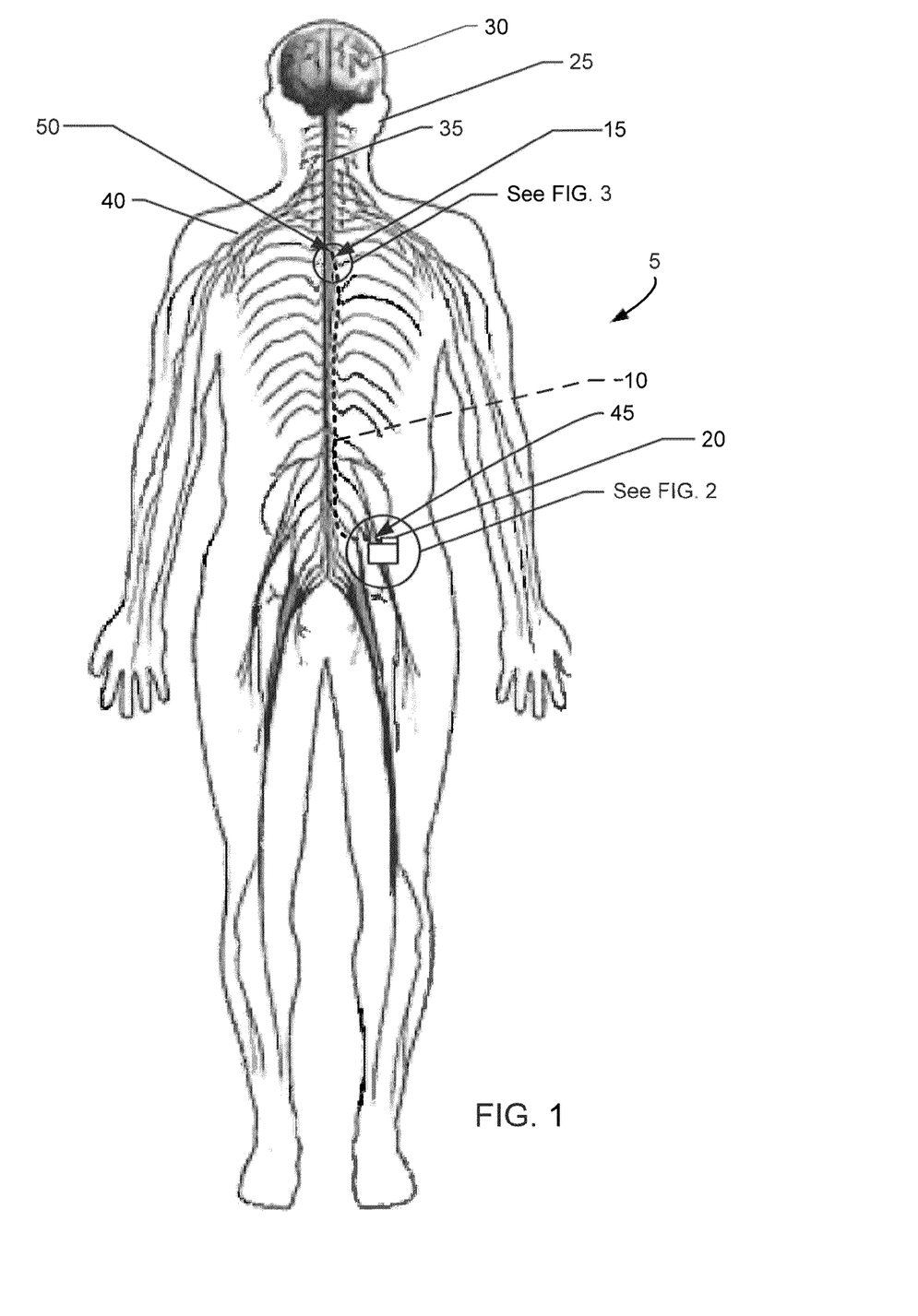
FIG. 1 is a diagrammatic depiction of a spinal cord stimulation (SCS) system implanted in a patient shown in posterior view.

To begin a general, non-limiting discussion regarding the SCS system 5 disclosed herein, reference is made to FIG. 1, which is a diagrammatic depiction of the SCS system 5 implanted in a patient 25 shown in posterior view. As shown in FIG. 1, the central nervous system of the patient 25 includes the brain 30 in the head of the patient, the spinal cord 35 extending through the spine of the patient, and the branch nerves 40 extending outward from the spinal cord.

As indicated in FIG. 1, the SCS system 5 includes a pulse generator 20 and a lead 10 having a proximal end 45 coupled to the pulse generator and extending distally away from the pulse generator to terminate in a lead distal end 50. The pulse generator 20 is configured to both sense nerve electrical signals and deliver electrical stimulation via the lead 10. While the SCS system 5 depicted in FIG. 1 is shown as having a single lead 10, depending on the needs of the patient, the SCS system 5 may employ multiple leads 10 having the configuration and capabilities described herein.

Figure 2:
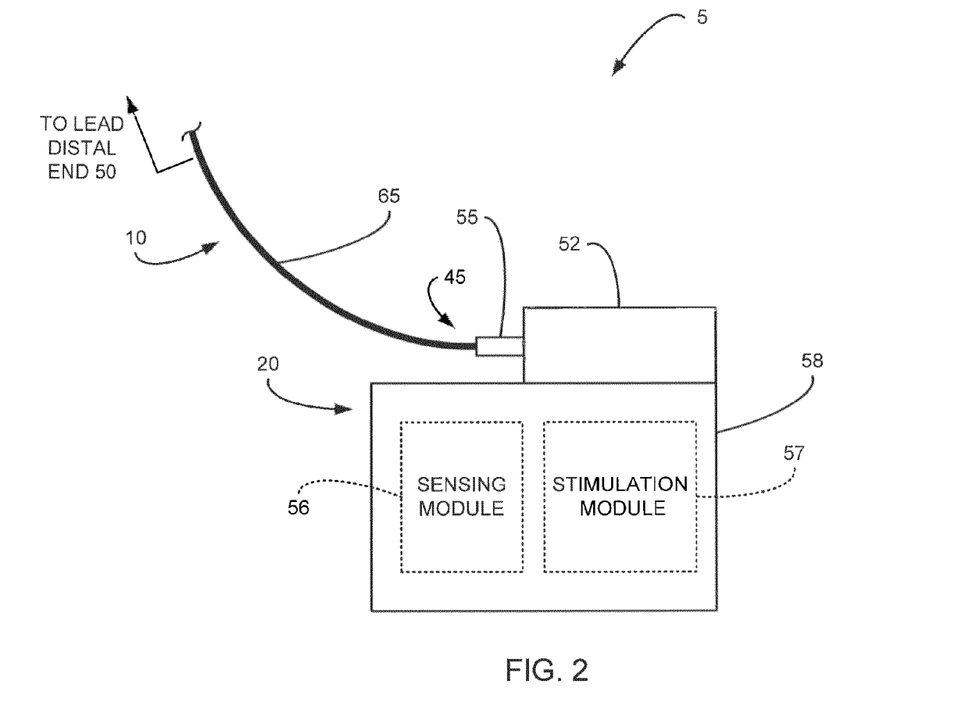
FIG. 2 is a side view of the pulse generator of the SCS system and the proximal end of the lead coupled thereto.

As indicated in FIG. 2, which is a side view of the pulse generator of the SCS system and the proximal end of the lead coupled thereto, the lead 10 is electrically coupled to a header 52 of the pulse generator 20 via a lead connector end 55 at the lead proximal end 45. As can be understood from FIG. 5 and discussed in greater detail below, electrical conductors 60 (e.g., wires, cables, helically coiled filars, etc.) extend through the lead body 65 from electrical contacts on the lead connector end to the various electrodes of the electrode array (s) on the distal region of the lead to electrically couple the various electrodes to electrical components (e.g., sensing module 56 and stimulation module 57) hermetically sealed in the housing or can 58 the pulse generator 20.

As illustrated in FIG. 1, in one embodiment, the SCS system 5 is implanted in the patient 30 such that the pulse generator 20 is implanted subcutaneously in a lower region of the patient torso, and the lead 10 is burrowed up through the patient back along the patient spine to have the lead distal end and the nearby electrode array(s) 15 located adjacent the nerves that are the target of the stimulation. For example, the lead 10 may extend up through the patient back from the pulse generator 20 until the lead enters the epidural space at T7 to have the electrodes near the therapy target site between T1 and T4. While the SCS system is shown as having the pulse generator in a lower region of the torso and the lead distal end in the thoracic vertebra region, the pulse generator may be implanted in other regions of the body and the lead distal end may be located to provide therapy to other locations on the central nervous system.

Figure 3:
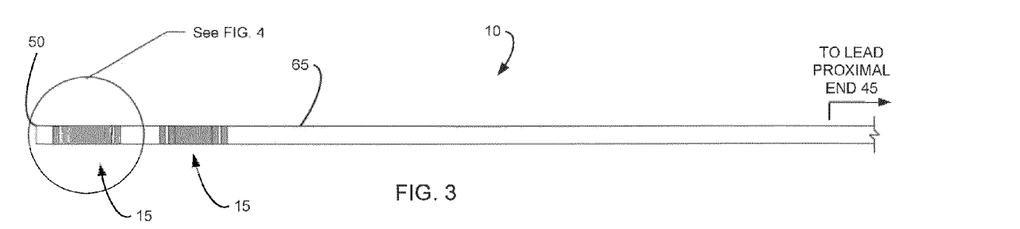
FIG. 3 is a side view of a distal portion of the implantable medical lead of the SCS system.

As shown in FIG. 3, which is a side view of a distal portion of the implantable medical lead 10 of the SCS system 5, the lead 10 includes a tubular body 65 and distally terminates at the distal end 50. The tubular body may be formed of silicone rubber, polyurethane, or silicone rubber polyurethane copolymer (SPC). The tubular body may have a size of between approximately 1 French and approximately 2 French.

One or more electrode arrays 15 are supported on the tubular body 65 near the distal end 50. Where there are multiple electrode arrays 15 on a single lead tubular body, the electrode arrays may be arranged in a spaced-apart fashion as depicted in FIG. 3.

Figure 4:
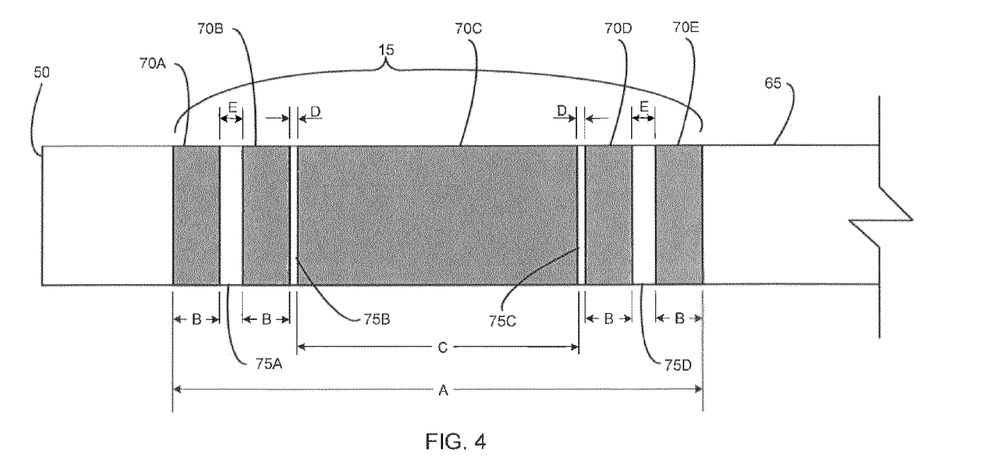
FIG. 4 is an enlarged view of an electrode region of the distal portion of the implantable medical lead.

As indicated in FIG. 4, which is an enlarged view of an electrode region of the distal portion of the implantable medical lead, an electrode array 15 may be in the form of a ring electrode 15 segmented into sub-ring electrodes 70A-E via circumferentially extending transverse cuts or spaces 75A-D. For example, in one embodiment, the ring electrode 15 is made up by two small distal electrodes 70A, 70B, one large middle electrode 70C, and two small proximal electrodes 70D, 70E.

As depicted in FIG. 4, in one embodiment, the large electrode 70C has a distal-proximal or longitudinal edge to edge length C of between approximately 1 mm and approximately 5 mm, with one specific embodiment having a length C of approximately 3.4 mm. Each small electrode 70A, 70B, 70D and 70E has a distal-proximal or longitudinal edge to edge length B of between approximately 0.1 mm and approximately 1.5 mm, with one specific embodiment having a length B of approximately 0.5 mm. In one embodiment, the length B of the small electrodes 70A, 70B, 70D and 70E may be sized according to sensing parameters needed for the specific target tissue, and the length C of the large electrode 70C may be sized according to stimulation parameters needed for the specific target tissue.

As shown in FIG. 4, in one embodiment, the two small distal electrodes 70A, 70B are separated from each other by an exposed space 75A of the tubular body 65 having a distal-proximal or longitudinal distance E between adjacent edges of the electrodes 70A, 70B of between approximately 0.05 mm and approximately 2 mm, with one specific embodiment having a distance E of approximately 0.2 mm. The most proximal small distal electrode 70B is separated from the large middle electrode 70C by an exposed space 75B of the tubular body 65 having a distal-proximal or longitudinal distance D between adjacent edges of the electrodes 70B, 70C of between approximately 0.02 mm and approximately 1 mm, with one specific embodiment having a distance D of approximately 0.1 mm. The most distal small proximal electrode 70D is separated from the large middle electrode 70C by an exposed space 75C of the tubular body 65 having distal-proximal or longitudinal distance D between adjacent edges of the electrodes 70C, 70D of between approximately 0.02 mm and approximately 1 mm, with one specific embodiment having a distance D of approximately 0.1 mm. The two small proximal electrodes 70D, 70E are separated from each other by an exposed space 75D of the tubular body 65 having a distal-proximal or longitudinal distance E between adjacent edges of the electrodes 70D, 70E of between approximately 0.05 mm and approximately 2 mm, with one specific embodiment having a distance E of approximately 0.2 mm. In one embodiment, the distances D may be minimized as much as possible in view of manufacturing constraints, and the distances E can be determined from the electrical conduction velocity of the target nerve.

As can be understood from the preceding discussion and FIG. 4, in one embodiment, the electrode array 15 has a distal-proximal or longitudinal edge to edge overall length A of between approximately 1.5 mm and approximately 17 mm, with one specific embodiment having an overall length A of approximately 6 mm. In one embodiment, the overall length A of the electrode array 15 may be sized according to stimulation parameters needed for the specific target tissue.

In one embodiment, the electrodes 70A-70E are made of platinum, platinum-iridium alloy, MP35N, etc. In one embodiment, the electrodes 70A-70E are positioned on the lead tubular body 65 as a single electrode 15 having a unitary structure and then segmented into the arrangement of sub-electrodes 70A-70E via laser cutting, micro-machining, etc. In other embodiments, the electrodes 70A-70E are positioned on the lead tubular body 65 individually or as a group of individual electrodes 70A-70E.

Figure 5:
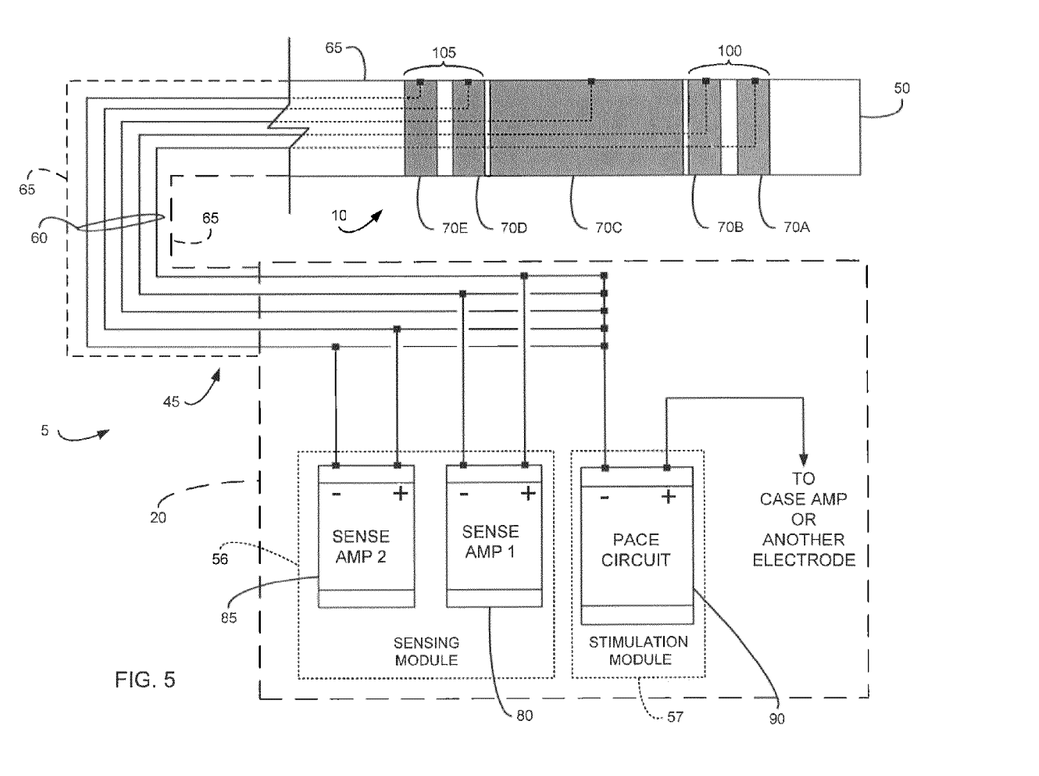
FIG. 5 is a diagrammatic depiction of the circuitry of the SCS system.

As can be understood from FIG. 5, which is a diagrammatic depiction of the circuitry of the SCS system 5, in one embodiment, the sensing module 56 in the pulse generator 20 includes a first sensing amplifier 80 and a second sensing amplifier 85. The stimulation module 57 in the pulse generator 20 also includes a pace circuit 90.

As illustrated in FIG. 5, the most distal electrode 70A of the small distal electrodes is electrically coupled via one of the conductors 60 to the negative side of the first sensing amplifier 80, and the most proximal electrode 70B of the small distal electrodes is electrically coupled via one of the conductors 60 to the positive side of the first sensing amplifier 80. As a result, the two small distal electrodes 70A, 70B for a distal bipole 100.

The most distal electrode 70D of the small proximal electrodes is electrically coupled via one of the conductors 60 to the negative side of the second sensing amplifier 85, and the most proximal electrode 70E of the small proximal electrodes is electrically coupled via one of the conductors 60 to the positive side of the second sensing amplifier 85. As a result, the two small proximal electrodes 70D, 70E for a proximal bipole 105.

Each of the small electrodes 70A, 70B, 70D and 70E is also electrically coupled via their respective conductors 60 to the negative side of the pace circuit 90. The large electrode 70C is also electrically coupled via one of the conductors 60 to the negative side of the pace circuit 90, but not to any of the sensing amplifiers 80, 85.

The special electrodes and electronics disclosed herein with respect to the SCS system 5 can provide the accurate neural signal sensing with good signal to noise ratio that is desirable for SCS. Specifically, to record nerve activity within the spinal column, one embodiment of the SCS system 5 disclosed herein is configured to have a passband of approximately 100 Hz to approximately 2 kHz and a sampling frequency of at least approximately 4 kHz to avoid aliasing (Nyquist frequency). As the nerve signals are very low amplitude, the SCS system 5 disclosed herein is configured to have a high gain (e.g., in order of 100× to 1000× amplification), which greatly increases the sensitivity of the sense circuit to noise.

Individual nerve fibers in the spinal column are on the order of 5-20 microns in diameter and can be very long. However, they have a myelin sheath which acts as an insulator from electrodes located in the epidural space. Thus, the electrode array 15 of the SCS system 5 disclosed herein has multiple small electrodes 70A, 70B, 70D and 70 with tight bipolar spacing and high impedance in order to achieve the spatial resolution needed to distinguish local neural firings.

In one embodiment, the sensing module 56 depicted in FIG. 5 has a passband of between approximately 100 Hz and approximately 2000 Hz, a sampling frequency of approximately 4000 Hz, and a gain of 500. In one embodiment, the SCS system 5 is configured to have multiplexing available or, alternatively, multiple sensing channels that may be simultaneously or selectively recorded.

As explained above with respect to FIGS. 1 and 4, the SCS system 5 disclosed herein utilizes a segmented ring electrode array 15 to provide SCS to the spinal column. In one embodiment, the segmented ring electrode array 15 is isodiametric with the tubular body 65 of the implantable medical lead 10, the tubular body 65 and electrode array 15 both having a size of approximately 1 French to approximately 2 French. In one embodiment, the segmented ring electrode array 15 may have a length A between its extreme distal and proximal edges of approximately 6 mm. The most distal 1.2 mm of the 6 mm overall length A of the electrode array 15 is made up of the two most distal ring electrodes 70A, 70B and the space 75A separating the two ring electrodes 70A, 70B. Specifically, the two most distal ring electrodes 70A, 70B of the segmented ring electrode array 15 each have a length B between extreme distal and proximal edges of approximately 0.5 mm and are separated from each other by the space 75A having a proximal-distal distance E of approximately 0.2 mm. The most proximal 1.2 mm of the 6 mm overall length A of the electrode array 15 is made up of the two most proximal ring electrodes 70D, 70E and the space 75D separating the two ring electrodes 70D, 70E. Specifically, the two most proximal ring electrodes 70D, 70E of the segmented ring electrode array 15 each have a length B between extreme distal and proximal edges of approximately 0.5 mm and are separated from each other by the space 75D having a proximal-distal distance E of approximately 0.2 mm. Each set of distal electrodes 75A, 75B and proximal electrodes 75D, 75E are separated from a middle large electrode 75C by a distal space 75B and a proximal space 75C which each have a distance C of approximately 0.1 mm. The large middle electrode 70C has a length C between extreme distal and proximal edges of approximately 3.4 mm.

As can be understood from FIG. 5, the distal pair 100 of small ring electrodes 70A, 70B are respectively electrically coupled to the positive and negative sides of the first sensing amplifier 80, and the proximal pair 105 of small ring electrodes 70B, 70D are respectively electrically coupled to the positive and negative sides of the second sensing amplifier 85. On account of their size, spacing, and being paired across one of two sensing amplifiers 80, 85, the pairs 100, 105 of small ring electrodes 70A, 70B, 70D, 70E can be used for very local sensing of neural activity. Since all of the small and large electrodes 70A-70E are electrically coupled to the pace circuit 90, all of the electrodes 70A-70E of the electrode array 15 can be used together as a single electrode 15 during stimulation in order to create an electrode 15 of substantial size and intermediate impedance that is appropriate for delivering spinal cord stimulation pulses. Because of the bipole electrode pairs 100, 105, the SCS system 5 is able to determine both direction and conduction velocity of nerve impulses. The SCS system 5 is also able to determine whether nerve impulse signals originate from dorsal or ventral spinal tracts.

In some embodiments, the electrode array 15 can have a configuration with an overall length A chosen to generally match with conventional percutaneous electrode lengths in order to keep delivery of stimulation consistent with current practice, while the lengths of the distal and proximal segment electrodes 70A, 70B, 70D, 70E are chosen in order to provide a very sharply local nerve signal with excellent common mode rejection from other signals such as ambient noise, cardiac signals, myopotentials, etc.

In some embodiments, as indicated in FIG. 3, the lead 10 may have multiple electrode arrays 15. One of the arrays 15 may have a configuration that is different from the other electrode array 15. For example, it may be desirable to have a lead 10 with arrays 15 with different combinations of overall length A, sensing segment length B, and bipolar segment spacing E (see FIG. 4 for lengths and spacing) in order to achieve specific objectives such as, for example, distinguishing between (or selectively sensing/rejecting) signals from alpha fibers, beta fibers, or gamma fibers, or for providing broader or narrower field stimulation within the spinal column. Further alternately, the sensing segment electrodes 70A, 70B, 70C, 70E may be omitted at either the proximal or distal portion of the overall electrode 15, such that only a single sense pair of the possible two pairs 100, 105 of small electrodes 70A, 70B and 70D, 70E exists with the large electrode 70C for each electrode array 15, in an effort to minimize the necessary device hardware.

As can be understood from FIG. 5, at a sufficiently high sampling frequency, it may be possible to detect a difference in timing between the peak of an activation spike (neural impulse) between the distal and proximal small bipoles 100, 105 respectively operating off of the first sensing amplifier 80 and second sensing amplifier 85. Furthermore, for a lead 10 having multiple arrays 15 of such split-ring electrodes 70A-70E, a timing difference between distal and proximal electrodes on a single lead may also be detectable, especially when considering longer leads and greater distance between distal and proximal electrodes. By employing methods to compare the sequence and timing of distal and proximal spike detections, it is possible to determine whether a signal is afferent or efferent. Such determination can be used for various algorithms for which neural sensing might serve as input.

Figure 6:
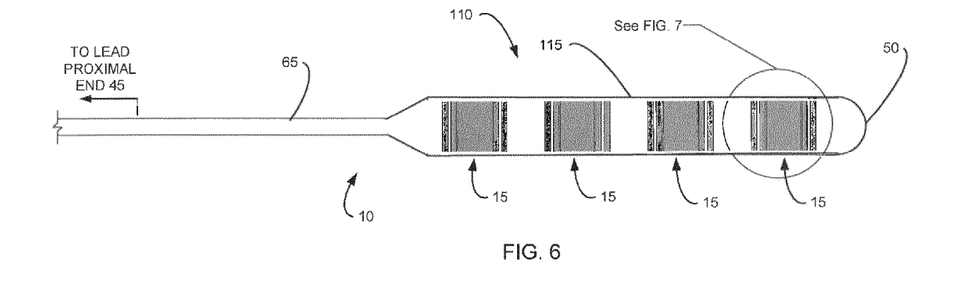
FIG. 6 is a distal portion of a paddle lead of the SCS system.

While the lead embodiments depicted in FIGS. 3 and 4 are of a percutaneous spinal cord lead 10 having a tubular body 65 generally along its entire length, a similar length and spacing configuration for each electrode array 15 can be applied to the flat electrodes 15 on a paddle lead 10 as illustrated in FIG. 6, which is a distal portion of a paddle lead. Such paddle leads are typically implanted by a laminotomy procedure. The paddle lead includes a tubular body 65 that transitions into a distal paddle shaped region 110. The paddle region 110 includes one or more flat electrode arrays 15 spaced apart from each other along a side of the paddle 110.

Figure 7:
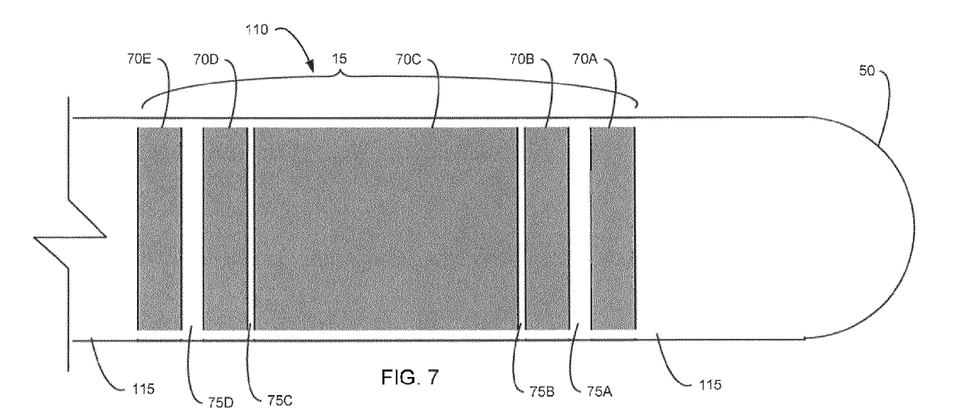
FIG. 7 is an enlarged view of an electrode array on the paddle of the paddle lead of FIG. 6.

As indicated in FIG. 7, which is an enlarged view of an electrode array 15 on the paddle 110 of the paddle lead 10 of FIG. 6, an electrode array 15 may be in the form of a flat electrode 15 segmented into sub electrodes 70A-E via transverse cuts or spaces 75A-D. For example, in one embodiment, the flat electrode 15 is made up by two small distal electrodes 70A, 70B, one large middle electrode 70C, and two small proximal electrodes 70D, 70E. The flat electrode array 15 of FIG. 7 may be electrically coupled to the sensing module 56 and stimulation module 57 as discussed above with respect to FIG. 5.

Figure 8:
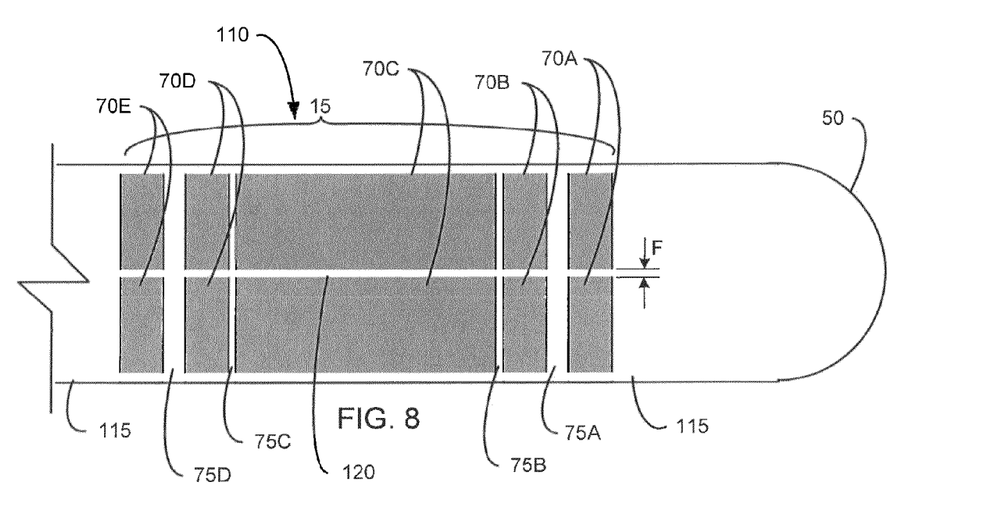
FIG. 8 is the same view as FIG. 7, except of another embodiment of the electrode array of the paddle of the paddle lead.

As can be understood from FIG. 8, which is the same view as FIG. 7, except of another embodiment, the electrode array(s) 15 of the paddle lead 10 may additionally be split along its longitudinal axis by a longitudinally extending space 120 such that there are lateral divisions of the electrode 15 in addition to longitudinal divisions of the electrode 15 as depicted in FIGS. 4 and 7. The longitudinally extending space 120 extends along the length of the electrode array 15, further segmenting each small electrode and large electrode 70A-70E into two transverse or lateral segments, as indicated in FIG. 8. In one embodiment, the longitudinally extending space has a side-to-side or transverse distance F between adjacent edges of the electrodes of between approximately 0.05 mm and approximately 2 mm, with one specific embodiment having a distance F of approximately 1 mm.

Such a transverse, in addition to longitudinal, segmenting of the electrode array 15 further allows bipolar sensing in a lateral orientation (i.e. transverse to the spinal cord axis). Such sensing is useful for determining how deep a nerve signal is in the spinal cord since neural action potentials will all be of approximately the same amplitude, and signals on a transverse bipolar recording electrode will appear larger if they are from the nerve fibers nearby (i.e. more dorsal) and will appear smaller in amplitude and of lower frequency content if originating from deeper fibers (i.e. more ventral). The relevance of determining dorsal versus ventral origination is that dorsal spinal cord fibers are typically associated with autonomic and sensory signals while ventral tracts are typically associated with motor signals.

As can be understood from FIGS. 4-7 and the preceding discussion, the system 5 and, specifically, the lead 10 and pulse generator 20, may be wired and controlled such that the small electrodes 70A, 70B, 70D, 70E and large electrode 70C act as a single electrode when stimulating. For example, in one embodiment, when the small electrodes and large electrodes act as a single electrode when stimulating, the small electrodes and large electrode may be caused to stimulate at exactly the same instance.

In another embodiment, when the small electrodes and large electrodes act as a single electrode when stimulating, the small electrodes and large electrode may be caused to stimulate such that the stimulating is staggered across the small and large electrodes with respect to time. Alternatively, the small electrodes and large electrode may be caused to stimulate such that the stimulating is staged across the small and large electrodes with respect to time.

In yet another embodiment, when the small electrodes and large electrodes act as a single electrode when stimulating, the small electrodes and large electrode may be caused to stimulate such that the stimulating occurs in different patterns across the small and large electrodes. For example, the stimulating may be caused to occur such that the stimulation pattern moves distal to proximal (or, alternatively, proximal to distal) in order along the small and large electrodes. In another embodiment, the stimulation pattern may be one of the following: the most distal electrode 70A followed by a most proximal electrode 70E followed by the next most distal electrode 70B followed by the next most proximal electrode 70D followed by the large electrode 70C In other words, the stimulation pattern leap-frogs distal-proximal in a narrowing pattern on the small electrodes until finishing with the center or large electrode 70C. Of course this pattern could be reversed or be any other pattern such as, for example, 75A to 75C to 75D to 75B. The possible patterns are very numerous, and all such patterns occur in a very short time period (e.g., several milliseconds) such that the various small and large electrodes can be considered to operating as a single electrode for purposes of stimulation.

Further, some patterns may include turning some of the electrodes of an array on while other electrodes of the array go off, or turning some of the electrodes of the array on at different times but leaving the electrodes on once turned on. Of course, all of this sequencing with respect to turning on (or on and off) occurs in a very short time period (e.g., several milliseconds) such that the various small and large electrodes can be considered to operate as a single electrode for purposes of stimulation.

In some embodiments, when the small electrodes and large electrodes act as a single electrode when stimulating, the small electrodes and large electrode stimulate exactly the same with respect to electrical characteristics such as voltage, current, amplitude, frequency, etc. Alternatively, when the small electrodes and large electrodes act as a single electrode when stimulating, the small electrodes and large electrode stimulate differently with respect to electrical characteristics such as voltage, current, amplitude, frequency, etc.

While the electrode array configurations and operation disclosed herein is given in the context of implantable tubular lead bodies and implantable paddle lead bodies, of course, the electrode array configurations and operation are equally applicable to other lead body types as uses. Accordingly, the disclosure provided herein regarding the electrode array configurations and operations should not be construed to being limited to implantable tubular lead bodies or implantable paddle lead bodies.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A nerve stimulation system comprising:
an implantable pulse generator comprising a sensing module and a pace circuit; and
an implantable lead comprising a distal end, an electrode array near the distal end, a proximal end including a lead connector end configured to couple the proximal end to the pulse generator, and conductors extending through the lead from the electrode array and caused to be in electrical communication with the sensing module and pace circuit when the proximal end is coupled to the pulse generator,
wherein the electrode array comprises at least a first pair of small electrodes and a large electrode in close proximity to each other, the small electrodes and large electrode physically separated from each other by non-conductive spaces extending generally transversely to a longitudinal axis of the lead,
wherein, when the conductors are in electrical communication with the sensing module and pace circuit, the first pair of small electrodes are in electrical communication with both the sensing module and the pace circuit and the large electrode is in electrical communication with the pace circuit, but not the sensing module, and
wherein the system is configured for spinal cord stimulation and wherein the sensing module is configured to have: a passband of approximately 100 Hz to approximately 2 kHz, a sampling frequency of at least approximately 4 kHz, and a gain of approximately 100 to 1000.

2. The system of claim 1, wherein the small electrodes and large electrode function together during stimulation as a single electrode.

3. The system of claim 2, wherein each of the small electrodes has a length of between approximately 0.1 mm and approximately 1.5 mm and the large electrode has a length of between approximately 1 mm and approximately 5 mm.

4. The system of claim 1, wherein the first pair of small electrodes is distal or proximal of the large electrode.

5. The system of claim 1, wherein the electrode array further comprises a second pair of small electrodes and the sensing module includes a first sensing amplifier and a second sensing amplifier, wherein, when the conductors are in electrical communication with the sensing module and pace circuit, the first pair of small electrodes are electrically coupled across the first sensing amplifier and the second pair of small electrodes are electrically coupled across the second sensing amplifier and in electrical communication with the pace circuit.

6. The system of claim 5, wherein the length of the electrode array is approximately 6 mm.

7. The system of claim 1, wherein the first pair of small electrodes and the large electrode are each ring electrodes on a tubular body of the lead.

8. The system of claim 1, wherein the first pair of small electrodes and the large electrode are each generally planar electrodes on a paddle of a paddle lead.

9. The system of claim 8, wherein each small electrode of the first pair of small electrodes is segmented into sub-electrodes physically separated from each other by a non-conductive space extending generally parallel to a longitudinal axis of the lead.

10. The system of claim 1, wherein a distal-proximal distance across a non-conductive space between the small electrodes is between approximately 0.05 mm and approximately 2 mm.

11. The system of claim 10, wherein a distal-proximal distance across a non-conductive space between a small electrode and the large electrode is approximately 0.1 mm.

12. The system of claim 1, wherein a distal-proximal distance across a non-conductive space between a small electrode and the large electrode is between approximately 0.02 mm and approximately 1 mm.

13. The system of claim 12, wherein a distal-proximal distance across a non-conductive space between the small electrodes is approximately 0.2 mm.

14. The system of claim 1, wherein the sensing module is configured to have: a passband of approximately 100 Hz to approximately 2 kHz, a sampling frequency of approximately 4 kHz, and a gain of approximately 500.

15. The system of claim 1, wherein a distal-proximal distance across a non-conductive space between the small electrodes is approximately 0.2 mm and a distal-proximal distance across a non-conductive space between a small electrode and the large electrode is approximately 0.1 mm.

16. The system of claim 15, wherein each of the small electrodes has a length of between approximately 0.1 mm and approximately 1.5 mm and the large electrode has a length of between approximately 1 mm and approximately 5 mm.

* * * * *